United States Patent
Gallagher

(10) Patent No.: US 10,070,819 B2
(45) Date of Patent: Sep. 11, 2018

(54) SECURE CLIP WITH EASY OPERATION

(71) Applicant: SNUZA TRUST, Cape Town (ZA)

(72) Inventor: Gregory John Gallagher, Cape Town (ZA)

(73) Assignee: SNUZA TRUST, Cape Town (ZA)

( * ) Notice: Subject to any disclaimer, the term of this patent is extended or adjusted under 35 U.S.C. 154(b) by 0 days.

(21) Appl. No.: 15/509,396

(22) PCT Filed: Aug. 27, 2015

(86) PCT No.: PCT/IB2015/056493
§ 371 (c)(1),
(2) Date: Mar. 7, 2017

(87) PCT Pub. No.: WO2016/038494
PCT Pub. Date: Mar. 17, 2016

(65) Prior Publication Data
US 2017/0238874 A1    Aug. 24, 2017

(30) Foreign Application Priority Data

Sep. 8, 2014 (GB) .................................. 1415872.9

(51) Int. Cl.
A61B 5/00 (2006.01)
A61B 5/08 (2006.01)
A61F 13/49 (2006.01)
A45F 5/02 (2006.01)
A44B 99/00 (2010.01)

(52) U.S. Cl.
CPC ............ *A61B 5/6838* (2013.01); *A44B 99/00* (2013.01); *A45F 5/02* (2013.01); *A61B 5/08* (2013.01); *A61F 13/49* (2013.01)

(58) Field of Classification Search
CPC .. A44B 99/00; A45F 5/02; A61B 5/08; A61B 5/6838; A61F 13/49
See application file for complete search history.

(56) References Cited

U.S. PATENT DOCUMENTS 4,822,348 A * 4/1989 Casey .................... A61F 6/206
                                                        604/346
5,598,608 A * 2/1997 Naslund ............ B65D 33/1675
                                                        24/30.5 P (Continued)

FOREIGN PATENT DOCUMENTS

GB          2300925         11/1996
JP        2000253911         9/2000

OTHER PUBLICATIONS

International Search Report for PCT/IB2015/056493, dated Dec. 14, 2015.

(Continued)

Primary Examiner — David M Upchurch
(74) Attorney, Agent, or Firm — B. Aaron Schulman, Esq.; Stites & Harbison, PLLC

(57) ABSTRACT

A clip (10) is provided with a body (12,14) that can house a device (16) such as a breathing monitor and that can attach to a garment. The body (12,14) forms a fixed jaw (18) and has a pivot jaw (24) that can pivot to grip the garment between fixed jaw(18) and pivot jaw (24). The clip (10) also has a pivoting lock (38) with a detent (42) that locks the pivot jaw (24) in a closed position, when the lock (38) is in a lock position.

15 Claims, 6 Drawing Sheets

(56) References Cited

U.S. PATENT DOCUMENTS

| | | | | |
|---|---|---|---|---|
| 6,494,886 B1* | 12/2002 | Wilk | ................... | A61B 17/122 |
| | | | | 606/142 |
| 6,516,500 B2* | 2/2003 | Ogino | ..................... | A41F 11/06 |
| | | | | 24/504 |
| 2003/0101550 A1* | 6/2003 | Henry | .................. | A47F 5/0884 |
| | | | | 24/536 |
| 2004/0045133 A1 | 3/2004 | Buettell | | |
| 2008/0314941 A1* | 12/2008 | Knych | ...................... | A45F 5/02 |
| | | | | 224/191 |
| 2010/0201524 A1 | 8/2010 | Gallagher | | |
| 2011/0034820 A1 | 2/2011 | Pietersen | | |
| 2014/0345089 A1* | 11/2014 | Kaalberg | ............. | A47C 21/022 |
| | | | | 24/72.5 |
| 2015/0082585 A1* | 3/2015 | Mayberry | .............. | F41C 23/02 |
| | | | | 24/505 |

OTHER PUBLICATIONS

Written Opinion of the International Searching Authority for PCT/IB2015/056493, dated Dec. 14, 2015.

\* cited by examiner

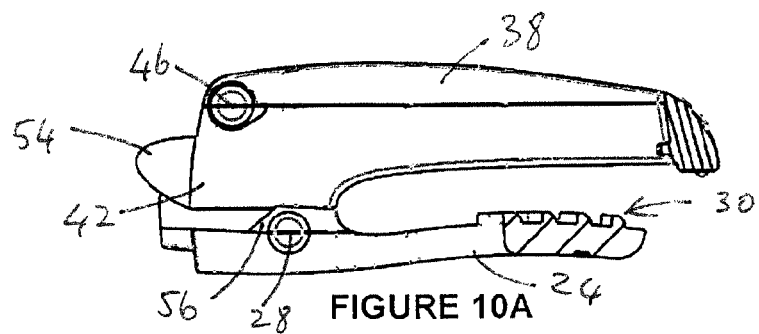
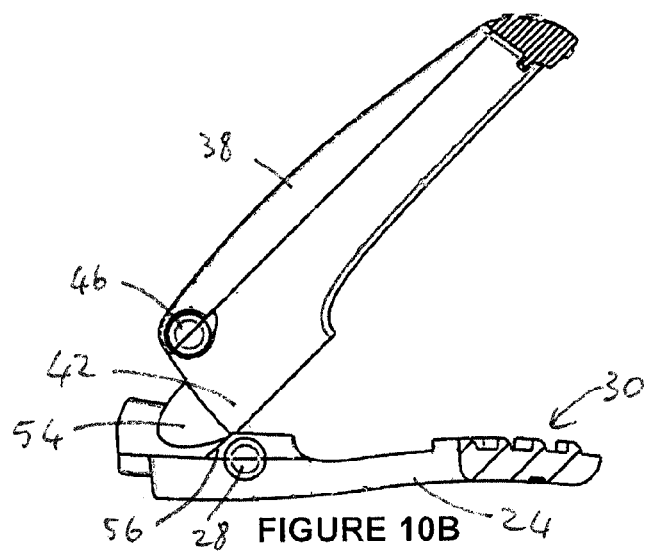
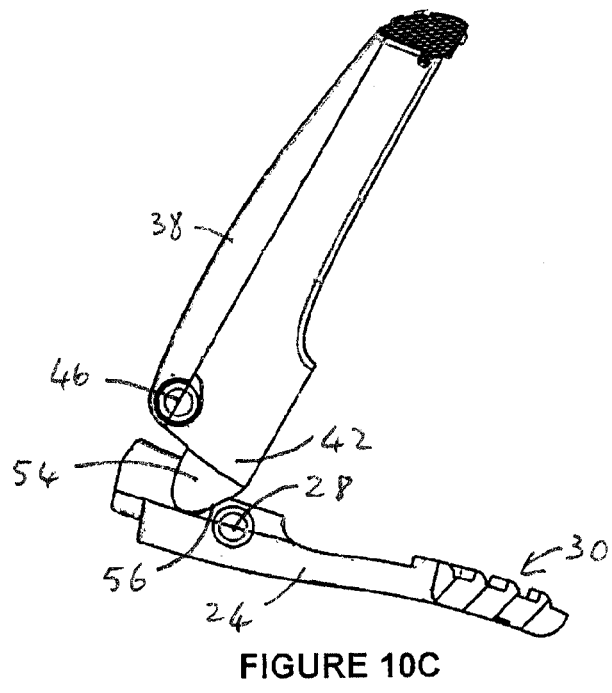

SECURE CLIP WITH EASY OPERATION

FIELD OF THE INVENTION

This invention relates to clips for the attachment of objects to garments and it is particularly suitable for attaching a breathing monitor to the waistband of an infant's diaper. The invention is described herein with reference to infant breathing monitors, but is by no means limited to such use. The invention can also be used for attachment of other objects to garments or to other substrates.

BACKGROUND TO THE INVENTION

Infant breathing monitors that are attached to the waistband of a diaper, or the like, need to be held in place securely, to ensure reliable functioning of the breathing monitor. However, the attachment and/or detachment of the monitor should be gentile enough not to disturb the infant. Further, infant breathing monitors are frequently used in poorly lit areas (where infants are expected to sleep) and the attachment and detachment of their breathing monitors should be simple and easy, to minimise the risk of incorrect attachment/detachment which could result in waking the infant and/or poor functioning of the monitor (with a likely false alarm that wakes the infant).

The present invention seeks to provide a clip for attaching an object (a breathing monitor or other object) to a substrate (a garment or other substrate) in a way that is simple and easy and requires little force yet secures the object to the substrate.

SUMMARY OF THE INVENTION

According to the present invention there is provided a clip for attachment to a substrate, said clip comprising:
   a body defining a fixed jaw;
   a pivot jaw that is pivotally attached to the body, to pivot relative to the body about a jaw axis, between a closed position in which a grip portion of the pivot jaw is in close proximity to the body, and an open position in which the grip portion is spaced farther from the body than in the closed position, said pivot jaw including a contact protuberance that extends on a side of the jaw axis, opposite from the grip portion, said contact protuberance defining a contact surface; and
   a lock that defines a detent, said lock being pivotally attached to the body, to pivot relative to the body about a lock axis, and said detent being configured to contact the contact surface at a contact point, at least occasionally, with a detent axis extending between the lock axis and the contact point and with a contact angle being defined between the detent axis and the contact surface, on the same side of the detent axis as the grip portion;
   wherein the lock is configured to pivot about the lock axis between a lock position in which the contact angle is an acute angle and a free position in which the contact angle is an obtuse angle.

The term "fixed" is used herein to distinguish between the two jaws by reference to their ability to pivot relative to the body. The term is not used in a narrow sense that would imply general immovability.

The term "close proximity" as used herein includes full contact between the grip portion and the fixed jaw.

The term "acute angle" is used herein to include a right angle, i.e. an acute angle is 90 degrees or less and an "obtuse angle" is more than 90 degrees.

The fixed jaw may include a grip protuberance and the pivot jaw may include at least two grip portions that are disposed on opposing sides of the grip protuberance. The pivot jaw may include a contact protuberance extending from each grip portion and the lock may include at least two detents that are configured to contact the contact surfaces of the contact protuberances in unison.

Instead, or in addition, the pivot jaw may include two contact protuberances that are disposed on opposing sides of the body and the lock may include two detents that are disposed on opposing sides of the body, to contact the contact surfaces of the contact protuberance in unison. The lock may extend in a curved configuration with the two detents disposed in the vicinities of opposing ends of the lock.

The body may house an electronic device to be worn on the person of a user and the electronic device may include a monitor for at least one biological parameter of the user, such breathing rate, temperature, orientation, heart rate, or the like.

Formations may be defined on the lock and on the pivot jaw, that interact when the lock is pivoted in an open direction about the lock axis, to pivot the pivot jaw in the open direction, away from the body.

BRIEF DESCRIPTION OF THE DRAWINGS

For a better understanding of the present invention, and to show how it may be carried into effect, the invention will now be described by way of non-limiting example, with reference to the accompanying drawings in which:

FIGS. 10A to 10C are detail sectional right side views of a pivot jaw and lock of the clip of FIG. 7, in progressive phases of releasing the clip and opening the pivot jaw.

DETAILED DESCRIPTION OF THE DRAWINGS

Figure 1:
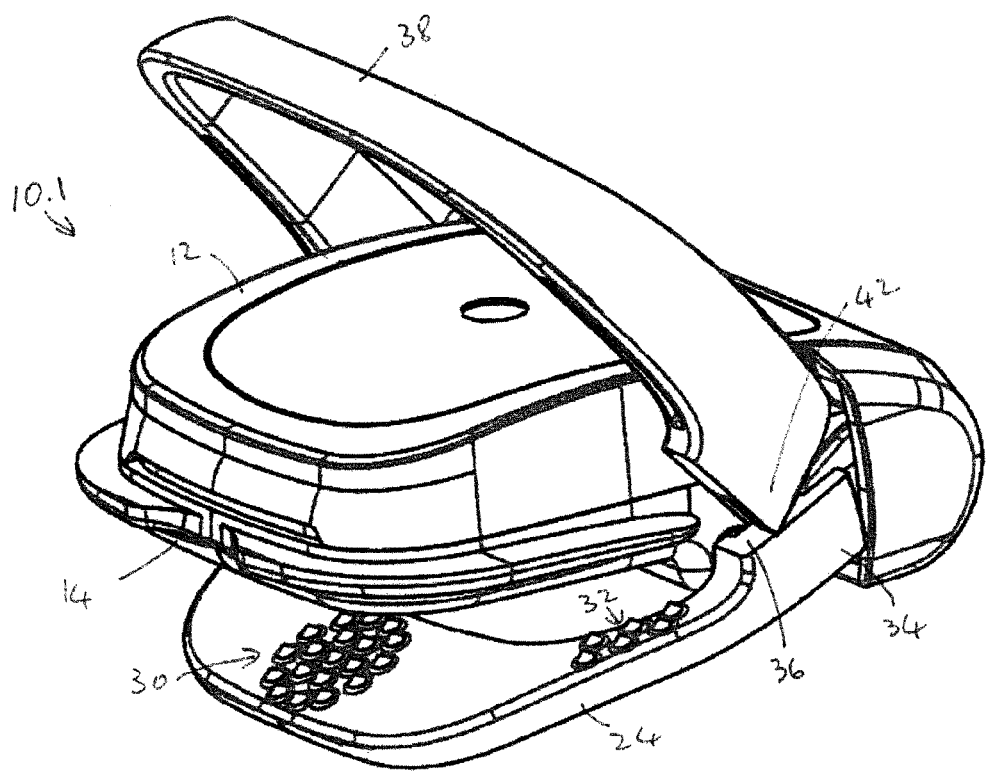
FIG. 1 is a three-dimensional view of a first embodiment of a clip according to the present invention, in an open condition.
Figure 2:
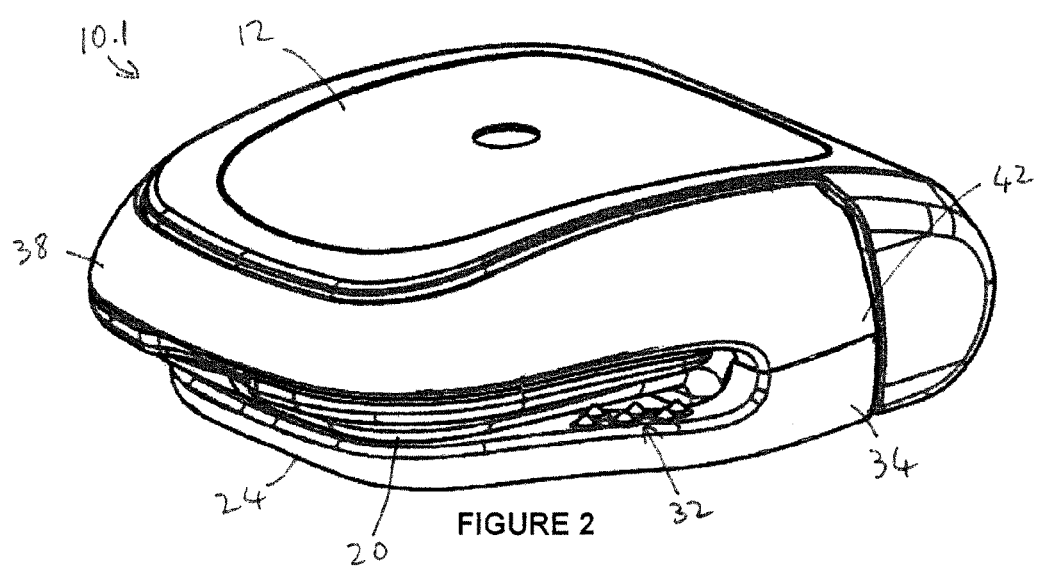
FIG. 2 is a three-dimensional view of the clip of FIG. 1 in a closed condition.

Referring to the drawings, a clip according to the present invention is generally identified by reference number 10 and different embodiments of the clip are identified by suffixes. Features that are common between different embodiments of the clip are identified by the same reference number.

Referring to FIGS. 1 to 6, the first embodiment of the clip 10.1 includes a body that in the illustrated example comprises an upper housing 12 and a lower housing 14, but the body can have comprise various other configurations, forming a housing. Inside the housing 12,14, there is electronic circuitry that makes up an electronic device that in the illustrated example is an infant breathing monitor 16 that needs to be worn on the person of the user (infant), for monitoring biological parameters of the user such breathing rate, temperature, orientation, heart rate, or the like. In other embodiments of the invention, different electronic circuitry may be used depending on the function of the device e.g. the circuitry may form part of a pedometer or a portable media player. The substrate to which the clip 10.1 is intended to be attached, is the waistband of the user's diaper. However, in other embodiments, the clip 10.1 can be used to attach other objects and/or to attach objects to other substrates such as other clothing or webbing.

The lower housing 14 defines a fixed jaw 18 that includes a wide central grip protuberance 20 and on opposing sides of the lower housing, two jaw axle recesses 22 are defined. The grip protuberance 20 enhances grip in this embodiment, by complementing the C-shape of the pivot jaw (see below), but in other embodiments, the lower housing 14 may be shaped differently.

The clip 10.1 includes a pivot jaw 24 that in this embodiment, has a curved, jaw-like shape with two truncated, inwardly facing jaw axles 26 that are received in the jaw axle recesses 22 of the lower housing 14, so that the pivot jaw can pivot relative to the lower housing about a jaw axis 28, which is the common axis of the jaw axles 26. The shape of the pivot jaw 24 can be different, as long as it complements the shape of the lower housing 14 adequately to grip a substrate. Further, in other embodiments, the pivot jaw could have any number of two jaw axles even only a single jaw axle.

The pivot jaw 24 preferably has a number of grip portions that extend along its curved shape, including an end grip portion 30 and two lateral grip portions 32 that are disposed on opposing sides of the grip protuberance 20 of the lower housing 14. The grip portions 30,32 preferably include grip-enhancing protuberances. The pivot jaw 24 can pivot about the jaw axis 28 between a closed position (shown in FIGS. 2 and 4) in which the grip portions 30,32, or other parts of the pivot jaw, are in close proximity to the lower housing 14 and an open position (shown in FIGS. 1 and 3) in which the grip portions are spaced farther from the lower housing than in the closed position. Depending on the thickness and compressibility of the substrate to which the clip 10 is to be attached and on the flexibility of the pivot jaw 24, the grip portions 30,32 may press against the lower housing 14 in the closed position, or they may be spaced slightly apart as long as adequate grip on the substrate is achieved (see below).

The pivot jaw 24 has at least one, but preferably two contact protuberances 34 that extend from each lateral grip portion 32 on a side of the jaw axis 28 that is opposite from the grip portions 30,32 (i.e. the contact protuberances extend to the rear, or to the right as shown in the drawings). Each of the contact protuberances 34 defines a contact surface 36 at its top.

The clip 10.1 includes a lock 38 that, in the illustrated embodiment extends in a curved, C-shaped configuration and in the vicinity of each of the opposing ends of the lock, it has an inwardly extending, truncated lock axle 40 and a protuberance that forms a detent 42. Like with the pivot jaw 24, the lock 38 can have a variety of other shapes and need not have two lock axles. The upper housing 12 defines two lock recesses 44 in which the lock axles 40 are received, so that the lock 38 can pivot relative to the upper housing 12 about a lock axis 46 that is the common axis of the lock axles.

Each of the detents 42 is configured to contact one of the contact surfaces 36 of the pivot jaw 24 at a contact point 48. Depending on the pivotal positions of the pivot jaw 24 and the lock 38, the detents 42 may not be in continual contact with the contact surfaces 36, but they are able to make contact at the contact point 48 at any time. In particular, there may be a small space between the grip portions 30,32 and the lower housing 14 when the pivot jaw 24 is in its closed position which space would be occupied by the substrate, when the clip 10 has been attached to a substrate. However, when the clip 10 is not attached to a substrate, the pivot jaw 24 may be able to pivot slightly beyond its closed position and contact between the detents 42 and contact surfaces 36 could be temporarily lost.

The housings 12,14, pivot jaw 24 and lock 38 are symmetrical and accordingly, the two detents 42 move in unison when the lock is pivoted about the lock axis 46 and the contact protuberances 34 move in unison when the pivot jaw 24 is pivoted about the jaw axis 28. Accordingly, the detents 42 on both sides of the clip 10 contact the contact surfaces 36 of the pivot jaw 24 in unison.

Figure 3:
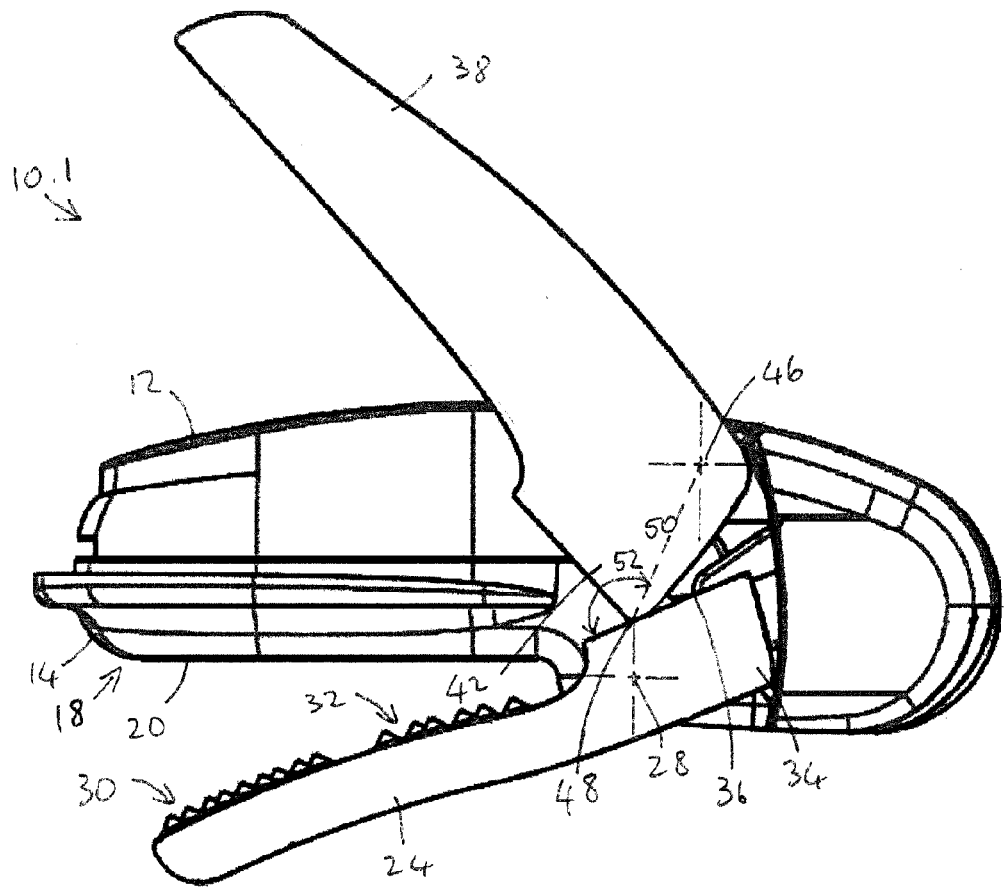
FIG. 3 is a left side view of the clip of FIG. 1 in the open condition.
Figure 4:
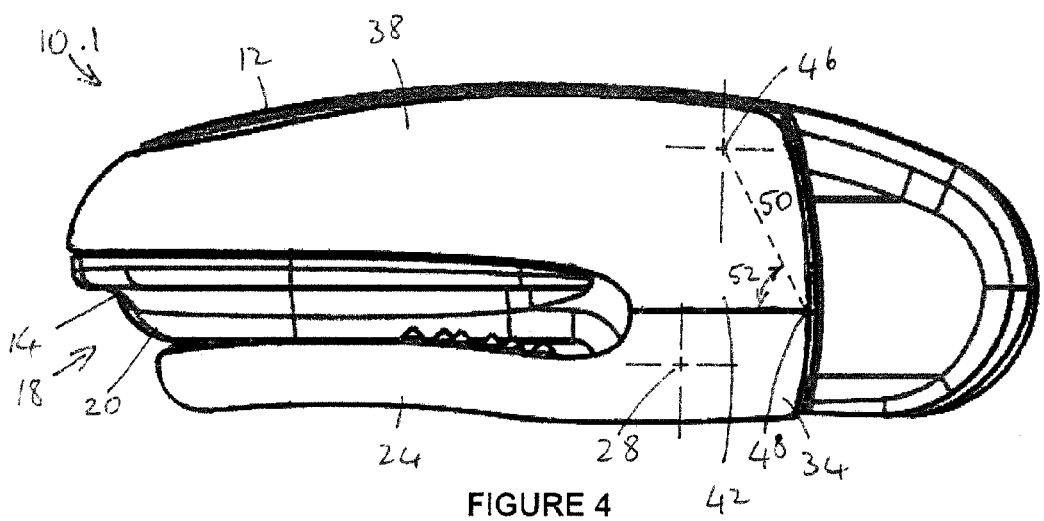
FIG. 4 is a left side view of the clip of FIG. 1 in the closed condition.
Figure 5:
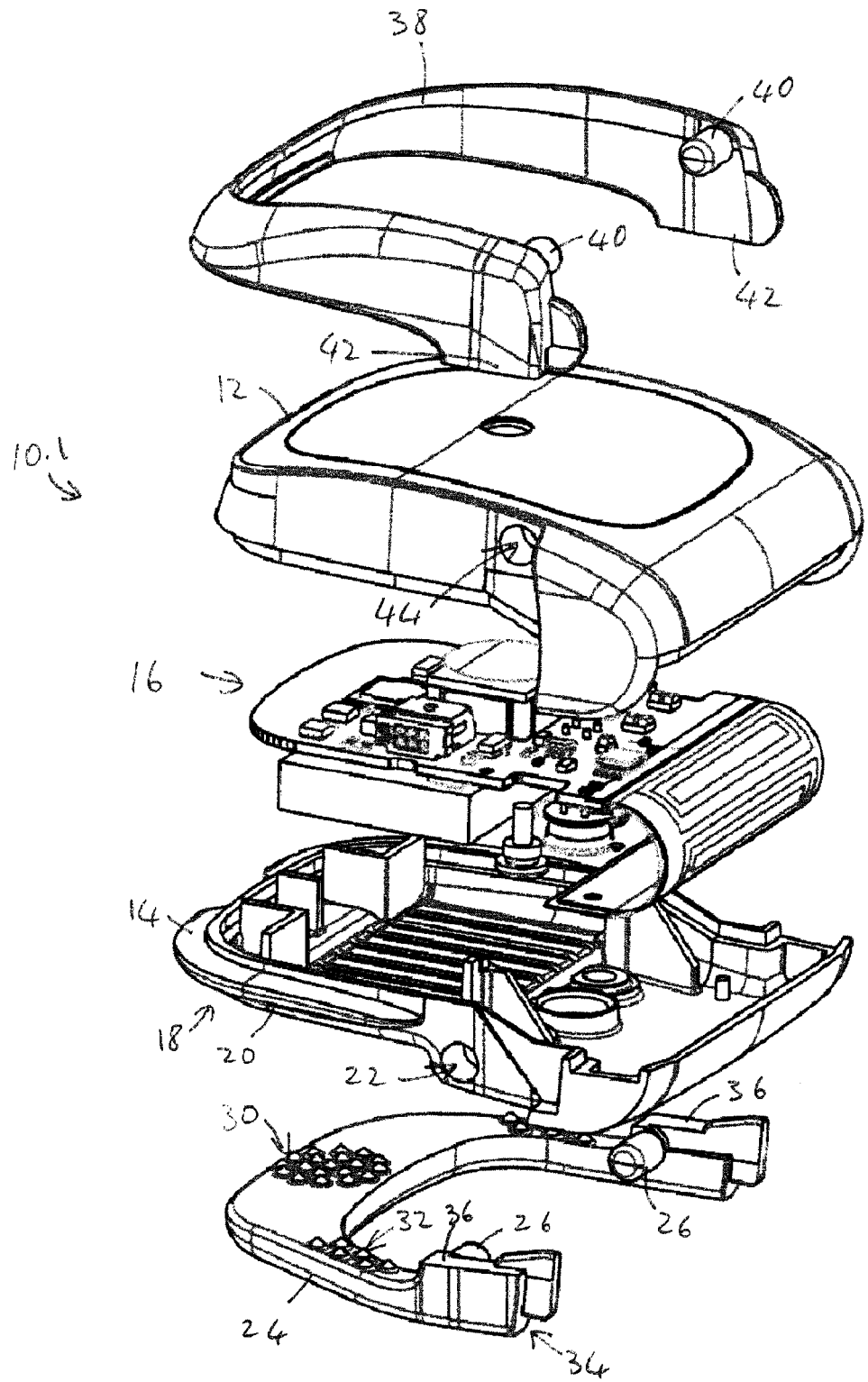
FIG. 5 is a rear three-dimensional, exploded view of the clip of FIG. 1.
Figure 6:
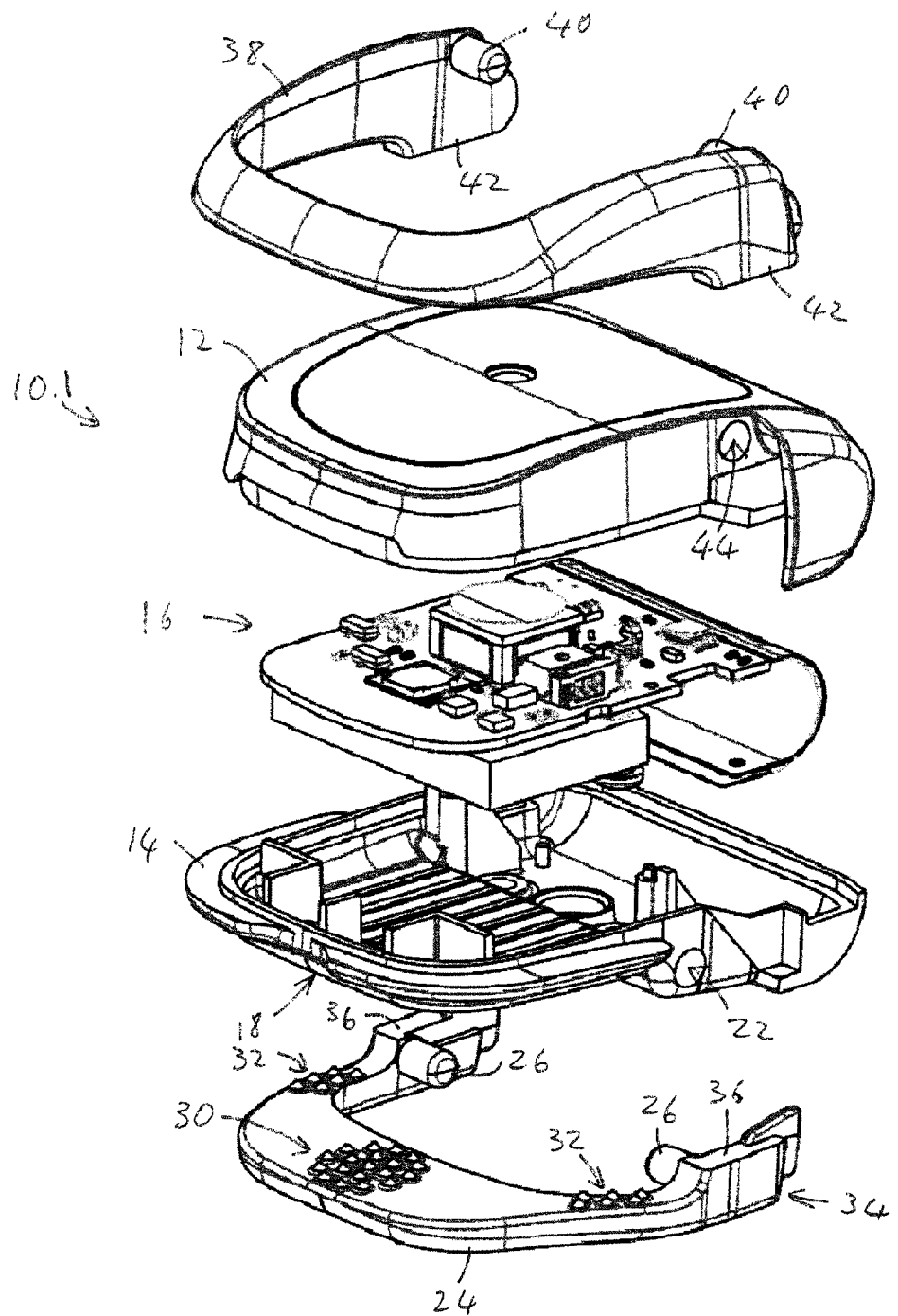
FIG. 6 is a front three-dimensional, exploded view of the clip of FIG. 1.
Figure 7:
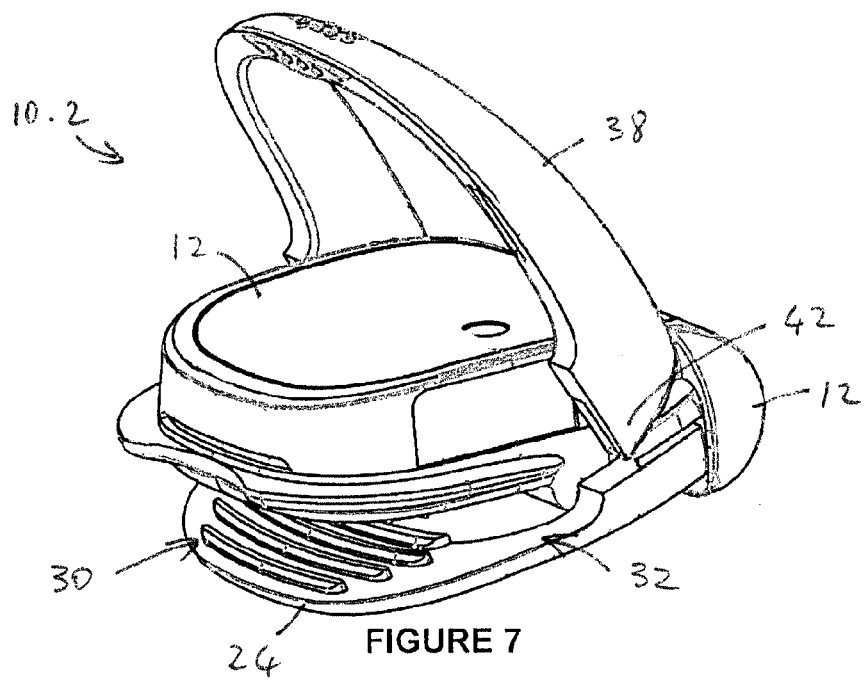
FIG. 7 is a three-dimensional view of a second embodiment of a clip according to the present invention, in an open condition.
Figure 8:
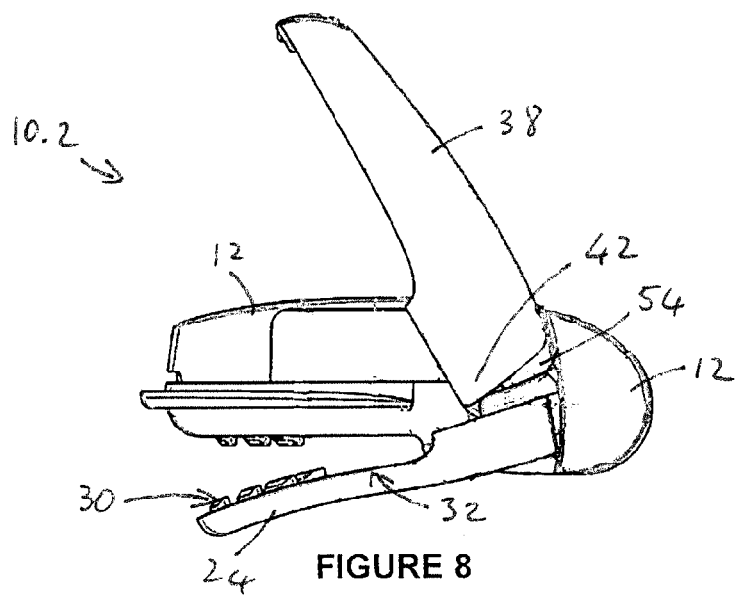
FIG. 8 is a left side view of the clip of FIG. 7 in the open condition.
Figure 9:
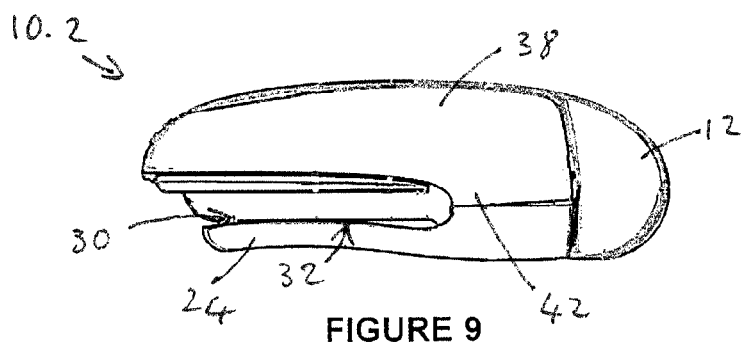
FIG. 9 is a left side view of the clip of FIG. 7 in a closed condition.

Even though other parts of the detents 42 may also be in contact with the contact surfaces 36, it is the contact point 48 that is furthest from the jaw axis 28 that is of particular interest in the present invention. A detent axis 50 extends on each side of the clip 10 between the lock axis 46 and the contact point 48 and intersects the contact surface 36 at a contact angle 52. The contact angle 52 is defined between the detent axis 50 and the contact surface 36 on the same side of the detent axis as the jaw axis 28 i.e. the contact angle is on the front, or left side of the detent axis, as shown in FIGS. 3 and 4.

The lock 38 can pivot about the lock axis 46 between a lock position (shown in FIGS. 2 and 4) in which the contact angle 52 is an acute angle and a free position (shown in FIGS. 1 and 3) in which the contact angle is an obtuse angle. The pivot jaw 24 and lock 38 are not mechanically linked to pivot together, but their pivotal movement from the free position of the lock and the open position of the pivot jaw, to the lock position of the lock and the closed position of the pivot jaw, and vice versa, occur at the same time, as will be described below.

In use, when the clip 10 needs to be attached to a substrate, the lock 38 is pivoted to its free position and the pivot jaw 24 is pivoted to its open position. The substrate is received with ease in the space between the grip portions 30,32 of the pivot jaw 24 and the lower housing 14.

In order to close the pivot jaw 24, the lock 38 is pivoted downwards, i.e. towards its lock position, by hand and during this pivotal movement, each detent 42 slides along its associated contact surface 36 so that the contact point 48 moves farther from the jaw axis 28 and pressure from the detent on the contact surface causes the pivot jaw 24 to pivot towards its closed position.

As the contact point 48 moves along the contact surface, it reaches a neutral point where the detent axis 50 intersects the contact surface at a right angle (i.e. the contact angle is 90 degrees) and at this neutral point, the detent extends farthest from the lock axis 46 towards the protuberance and exerts the greatest pressure on the contact surface. Accordingly, the pivot jaw 24 is urged most by the detent, at this neutral point, to pivot towards its closed position. Depending on the design of the clip 10, the grip portions 30,32 may be in near contact with the lower housing 14 at the neutral point, or may be spaced slightly farther, but the substrate would be compressed between the grip portions and the lower housing 14.

As the lock 38 is pivoted further towards its lock position, beyond its neutral position, the detents 42 slide along the contact surfaces 36, the contact points 48 move farther from the jaw axis 28, the contact angle becomes smaller (becomes acute) and the distance by which the detents extend from the lock axis 46 towards the contact surfaces 36, starts reducing. As a result, the pressure between the detents 42 and the contact surfaces 36 is reduced, until the lock 38 reaches its lock position.

While the lock 38 is in its lock position and retains the pivot jaw 24 in its closed position, the substrate is pinched between the pivot jaw 24 and the fixed jaw 18 of the lower housing 14. This pinching action is preferably enhanced by the fact that the central grip protuberance 20 extends downwards between the lateral grip portions 32, so that the substrate is tightly curved around the central protuberance.

If the lock 36 is pivoted from its lock position, the pivotal movement described above is reversed and increasing pressure is applied between the detents 42 and the contact surfaces 36 until the lock is pivoted the neutral position. The force required to overcome this resistance to pivotal movement of the lock 36 to the neutral position is small enough to be applied by hand, with ease, yet is large enough for it to be highly unlikely that such a force would be applied inadvertently, and the clip 10 released.

To release the clip 10, the lock 38 is pivoted by hand from its lock position, through its neutral position and to its free position. While the lock 38 pivots from its neutral position to its free position, the constraint exerted by the detents 42 on the contact surfaces is reduced and the pivot jaw 24 is allowed to open.

The manual operation that is required to attach the clip 10 to the substrate, or to release it, is simply the pivotal movement of the lock 38 between its lock and free positions. Further, the clip 10 can preferably be designed (as in the case of the illustrated embodiment) so that the pivotal rotation of the lock 38 is greater than the pivotal rotation of the pivot jaw 24 and accordingly, the pinching force exerted between the jaws 18,24 on the substrate, is greater than the manual force required to pivot the lock. The clip 10 is thus easy to operate, both in simplicity of operation and in the relatively small manual force required yet is attaches securely to the substrate.

Referring to FIGS. 7 to 10C, the second embodiment of the clip 10.2 is substantially the same as the first embodiment, shown in FIGS. 1 to 6, apart from minor differences in shape, e.g. having elongated protuberances at the end grip portion 30, instead of an array of small domes and having no protuberances in the lateral grip portions 32 on the pivot jaw 24.

One significant feature of the clip 10.2 is that the lock 38 has two cam elements 54 that protrude from its ends, adjacent the detents 42. The cam elements 54 are normally not clearly visible because they extend inside the upper housing 12, but the cam elements 54 are clearly visible in FIGS. 10A to 10C.

As shown in FIGS. 10A to 10C, when the lock 38 of the clip 10.2 is pivoted through about 45 degrees from the closed position shown in FIG. 10A to an intermediary position shown in FIG. 10B, the cam elements 54 do not cause the pivot jaw 24 to move (although pivotal movement of the pivot jaw is also not prevented). When the lock 38 is pivoted further in the open direction from an angle of about 45 degrees to an angle of about 60 degrees relative to its closed position, the cam elements 54 interact with cam follower surfaces 56 defined adjacent the contact surfaces 36 on the pivot jaw 24. The cam elements 54 press against the cam follower surfaces 56 in cam-fashion while the lock 38 is pivoted upwards and the cam-fashion pressure on the cam follower surfaces cause the pivot jaw 24 to pivot downwards, to its open position shown in FIG. 10C, where it is oriented at an angle of about 15 degrees relative to its closed position.

The provision of the cam elements 54 and cam follower surfaces 56 in the clip 10.2 thus provides active opening of the pivot jaw 24, in addition to the closing and locking action described above, with reference to FIGS. 1 to 6.

The positions of the cam elements 54 and cam follower surfaces 56 can be swapped around, between the lock 38 and pivot jaw 24, or instead, the lock and pivot jaw can have a variety of other formations, which interact when the lock is pivoted in the open direction, to pivot the pivot jaw in the open direction. Such alternative formations can interact in cam-fashion or in any other manner, e.g. a linkage can be provided between the lock 38 and the pivot jaw 24.

The invention claimed is:

1. A clip for attachment to a substrate, said clip comprising:
   a body defining a fixed jaw;
   a pivot jaw that is pivotally attached to the body, to pivot relative to the body about a jaw axis, between a closed position in which a grip portion of the pivot jaw is in close proximity to the body, and an open position in which the grip portion is spaced farther from the body than in the closed position, said pivot jaw including a contact protuberance that extends on a side of the jaw axis that is opposite from the grip portion, said contact protuberance defining a contact surface; and
   a lock that defines a detent, said lock being pivotally attached to the body, to pivot relative to the body about a lock axis, and said detent being configured to contact the contact surface at a contact point, with a detent axis extending between the lock axis and the contact point and with a contact angle being defined between the detent axis and the contact surface, on the same side of the detent axis as the grip portion;
   wherein the lock is configured to pivot about the lock axis between a lock position in which the contact angle is an acute angle and a free position in which the contact angle is an obtuse angle.

2. The clip according to claim 1, wherein the fixed jaw includes a grip protuberance and the pivot jaw includes at least two grip portions that are disposed on opposing sides of the grip protuberance.

3. The clip according to claim 2, wherein the pivot jaw includes a contact protuberance extending from each grip portion and the lock includes at least two detents that are configured to contact the contact surfaces of the contact protuberances in unison.

4. The clip according to claim 1, wherein the pivot jaw includes two contact protuberances that are disposed on opposing sides of the body and the lock includes two detents that are disposed on opposing sides of the body, to contact the contact surfaces of the contact protuberances in unison.

5. The clip according to claim 4, wherein the lock extends in a curved configuration with the two detent disposed in the vicinities of opposing ends of the lock.

6. The clip according to claim 1, wherein the body houses an electronic device to be worn on the person of a user.

7. The clip according to claim 6, wherein the electronic device includes a monitor for at least one biological parameter of the user.

8. The clip according to claim 1, in which formations are defined on the lock and on the pivot jaw, said formations interacting when the lock is pivoted in an open direction about the lock axis, to pivot the pivot jaw in the open direction, away from the body.

9. The clip according to claim 2, wherein the pivot jaw includes two contact protuberances that are disposed on opposing sides of the body and the lock includes two detents that are disposed on opposing sides of the body, to contact the contact surfaces of the contact protuberances in unison.

10. The clip according to claim 9, wherein the lock extends in a curved configuration with the two detents disposed in the vicinities of opposing ends of the lock.

11. The clip according to claim 3, wherein the pivot jaw includes two contact protuberances that are disposed on opposing sides of the body and the lock includes two detents that are disposed on opposing sides of the body, to contact the contact surfaces of the contact protuberances in unison.

12. The clip according to claim 11, wherein the lock extends in a curved configuration with the two detents disposed in the vicinities of opposing ends of the lock.

13. The clip according to claim 2, in which formations are defined on the lock and on the pivot jaw, said formations interacting when the lock is pivoted in an open direction about the lock axis, to pivot the pivot jaw in the open direction, away from the body.

14. The clip according to claim 3, in which formations are defined on the lock and on the pivot jaw, said formations interacting when the lock is pivoted in an open direction about the lock axis, to pivot the pivot jaw in the open direction, away from the body.

15. The clip according to claim 4, in which formations are defined on the lock and on the pivot jaw, said formations interacting when the lock is pivoted in an open direction about the lock axis, to pivot the pivot jaw in the open direction, away from the body.

* * * * *